(12) United States Patent
Ignatyev et al.

(10) Patent No.: US 8,106,217 B2
(45) Date of Patent: Jan. 31, 2012

(54) IONIC LIQUIDS WITH BIS[BIS(PENTAFLUOROALKYL)PHOSPHINYL]IMIDES

(75) Inventors: Nikolai (Mykola) Ignatyev, Duisburg (DE); Urs Welz-Biermann, Heppenheim (DE); Michael Heckmeier, Hemsbach (DE); German Bissky, Wuppertal (DE); Helge Willner, Muelheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 480 days.

(21) Appl. No.: 11/916,139

(22) PCT Filed: May 12, 2006

(86) PCT No.: PCT/EP2006/004485
§ 371 (c)(1),
(2), (4) Date: Nov. 30, 2007

(87) PCT Pub. No.: WO2006/128563
PCT Pub. Date: Dec. 7, 2006

(65) Prior Publication Data
US 2008/0194831 A1    Aug. 14, 2008

(30) Foreign Application Priority Data
Jun. 2, 2005 (DE) .......................... 10 2005 025 315

(51) Int. Cl.
C07D 207/06 (2006.01)
C07D 233/06 (2006.01)
C07D 233/08 (2006.01)
C07D 233/10 (2006.01)
C07D 213/06 (2006.01)

(52) U.S. Cl. ................. 548/335.1; 548/564; 546/347

(58) Field of Classification Search ............... 548/335.1, 548/564; 546/347
See application file for complete search history.

(56) References Cited

U.S. PATENT DOCUMENTS

| 6,682,855 | B2 | 1/2004 | Michot et al. |
| 2004/0199015 | A1 | 10/2004 | Yuyama et al. |
| 2005/0256334 | A1 | 11/2005 | Welz-Biermann et al. |
| 2007/0128515 | A1 | 6/2007 | Ignatyev et al. |
| 2007/0265453 | A1 | 11/2007 | Welz-Biermann et al. |

FOREIGN PATENT DOCUMENTS

WO     WO 03/087110 A     *  10/2003

OTHER PUBLICATIONS

Slattery et. al. "How to Predict the Physical Properties of Ionic Liquids: A Volume Based Approach" Angewandte Chemie Interntational Edition 2007, 46, 5384-5388.*
Welton et. al. Chemical Reviews 1999, 99, 2071-2083.*
Hagiwara, R. and Ito, Y., "Room temperature ionic liquids of alkylimidazolium cations and fluoroanions", J. Fluorine Chem. 105 (2), 221-227 (2000).*
N. V. Pavlenko et al. [Azotistnye proizvodnye bis(geptaftorpropyl)fosfinovoi kisloty] Nitrogen Derivatives of Bis(Heptafluoropropyl)Phosphinic Acid Zhurnal obshchei khimii 1984 vol. 55 No. 7 pp. 1586-1590 and translation.*
Journal of Fluorine Chemistry 131 (2010) 325-332—"New ionic liquids with the bis[bis(pentafluoroethyl)phosphinyl]imide anion, $[(C_2F_6)_2P(O)]^2$—Synthesis and characterization"—Dana Sejan et al.
XP-002399493—ChemPhysChem 2004, 5, 1106-1120—"Non-Haloaluminate Room-Temperature ionic Liquids in Electrochemistry—A Review"—Marisa C. Buzzeo et al.
XP-002399494—J. Am Chem. Soc. 1985, 107, 3719-3721—"Dependence of Rate Constants of Heterogeneous Electron Transfer Reactions on Viscosity"—X. Zhang et al.
Pavlenko, N.V., et al.; See Abstract; Database Beilstein (Online); XP002399496; Database Accession No. BRN 6764178. BRN 6766089; Journal of General Chemistry USSR; 1985; pp. 1410-1414, vol. 55, No. 7.
Inorg. Chem. 2008, 47, 9085-9089 Inorganic Chemistry Article—Inorganic Chemistry, vol. 47, No. 19, 2008—"Synthesis and Characterization of Bis[bis(pentafluoroethyl)phosphinyl]imides, $M^+N[(C_2F_5)_2P(O)]_2$, M=H, Na, K, Cs, Ag, $Me_4N^+$"—Dana Beim et al.
"Nitrogenous Derivatives of Bis(Heptafluoropropyl)Phosphinio Acid"—N.V. Pavlenko et al., © 1986 Plenum Publishing, pp. 1410-1414.
"Nitrogenous Derivatives of Bis(Heptafluoropropyl)Phosphinic Acid"—N.V. Pavlenko et al., © 1986 Plenum Publishing, pp. 1410-1414.

* cited by examiner

Primary Examiner — David K O Dell

(74) Attorney, Agent, or Firm — Millen, White, Zelano & Branigan, P.C.

(57) ABSTRACT

The present invention relates to ionic liquids of low viscosity and high electrochemical stability, in particular for use in the area of electrochemistry and as solvents for carrying out chemical reactions.

17 Claims, No Drawings

IONIC LIQUIDS WITH BIS[BIS(PENTAFLUOROALKYL)PHOSPHINYL]IMIDES

The present invention relates to ionic liquids of low viscosity and high electrochemical stability.

Ionic liquids or liquid salts are ionic species which consist of an organic cation and a generally inorganic anion. They do not comprise neutral molecules and usually have melting points below 373 K.

Intensive research is currently being carried out in the area of ionic liquids since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionic Flüssigkeiten—neue Lösungen füdie Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability and viscosity, are greatly influenced by the nature of the anion. By contrast, the polarity and hydrophilicity or lipophilicity can be varied through a suitable choice of the cation/anion pair.

The viscosity plays a major role, in particular, in applications in the area of electrochemistry and when selecting suitable solvents for carrying out chemical reactions. If the ionic liquid is too viscous, the diffusion of ions is too slow in electrochemical applications, and the electrochemical processes proceed too slowly. In the case of chemical reactions, the reduced mass-dependant mobility of the reactants in relatively viscous liquids results in a slowing of the reaction rate. A number of ionic liquids, for example containing $[N(CN)_2]$, $[N(CF_3)_2]$ or thiocyanate anions, of lower viscosity have been proposed for solving this problem. In spite of this advantage, however, the said systems are finding little practical application since their hydrolysis and thermal stability and their stability to oxidation and/or reduction are inadequate for these applications.

The object was therefore to develop ionic liquids which are suitable for use in electrochemical applications and as solvents for carrying out chemical reactions.

The invention accordingly relates to ionic liquids comprising cations and anions where the viscosity is 10 to 100 mm²/s and the electrochemical stability to reduction and oxidation (the electrochemical window) is greater than 4.5 V. The value of 4.5 V for the electrochemical stability is based on the entire electrochemical window, i.e. it spans the entire range from reduction to oxidation. Ionic liquids which meet this complex requirement profile are particularly suitable for use in electrochemical applications and in organic syntheses and thus allow access to novel reaction media for chemical processes.

In the present invention, the viscosity is the kinematic viscosity, which is given by the ratio of the dynamic viscosity and the density of the liquid. This viscosity is 10 to 100 mm²/s, preferably 20 to 60 mm²/s, in the ionic liquids according to the invention. The said limit ranges for the kinematic viscosity correspond to values of 10 to 170 mPa·s (cp) for the dynamic viscosity. In the present invention, the kinematic viscosity is determined using an Anton Paar SVM 3000 rotational viscometer and in accordance with the ASTM D7042 standard, "Standard Test Method for Dynamic Viscosity and Density of Liquids by Stabinger Viscometer (and the Calculation of Kinematic Viscosity)" from ASTM International.

The electrochemical stability is determined by cyclic voltammetry. For the purposes of the present invention, the measurement is carried out using an Autolab PGSTAT 30 instrument (Eco Chemie). The values for the electrochemical window indicated in the present invention were measured in 0.5 molar solution in $CH_3CN$ using a glassy-carbon electrode as working electrode, a platinum electrode and an $Ag/AgNO_3$ ($CH_3CN$) reference electrode. The potential values are based on $E^0$ of ferrocene.

In addition, the purity of the ionic liquid likewise plays a major role. In particular in the above-mentioned applications, the purity, i.e. the absence of impurities, is a crucial criterion for usability. The ionic liquids in accordance with the present invention preferably have a chloride content of less than 100 ppm. Ionic liquids which meet the requirements of viscosity, electrochemical stability and purity are particularly suitable for use in the above-mentioned applications. Indeed, it is only the combination of these parameters that enables improvements to be achieved with respect to uses in electrochemical applications or as solvent for chemical reactions.

In particular, ionic liquids satisfy the above-mentioned criteria if the anion conforms to the formula $[(R_F)_2P(O)]_2N^-$, where $R_F$ has the meaning

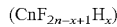

$(CnF_{2n-x+1}H_x)$ where n=1-6 and x=0-4, where, for n=1, x should be 0 to 2. $R_f$ preferably denotes $CF_3$, $C_2F_5$, $C_3F_7$ or $C_4F_9$. The anion is particularly preferably $[(C_2F_5)_2P(O)]_2N^-$.

Compounds containing chemically similar anions are mentioned in U.S. Pat. No. 6,682,855 as additional constituent in aprotic solvents for the preparation of ion-conducting materials, the compounds of U.S. Pat. No. 6,682,855 differing from the compounds according to the invention in that at least one fluorine atom must be bonded to the phosphorus in the case of the presence of perfluorinated alkyl groups. Due to the combination of these compounds with corresponding solvents, the viscosity of the said compounds does not play a role since the viscosity of the ion-conducting material is crucially determined by the solvent. In the present invention, by contrast, the viscosity of the ionic liquid plays a crucial role, in particular in the case of the use as novel reaction media for organic syntheses.

There are no restrictions per se with respect to the choice of the cation of the ionic liquid in accordance with the present invention. However, preference is given to organic cations, particularly preferably ammonium, phosphonium, uronium, thiouronium, guanidinium or heterocyclic cations.

Ammonium cations can be described, for example, by the formula (1)

$$[NR_4]^+ \qquad (1),$$

where
R in each case, independently of one another, denotes
H, with the proviso that at least two substituents R in the formula (1) are H, OR', $NR'_2$, with the proviso that at most one substituent R in the formula (1) is OR' or $NR'_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X or —NO$_2$, and where one or two non-adjacent carbon atoms of the R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' may be =H, non-, partially or perfluorinated $C_1$- to $C_6$-alkyl, $C_3$- to $C_7$-cycloalkyl, or unsubstituted or substituted phenyl, and X may be halogen.

Phosphonium cations can be described, for example, by the formula (2)

$$[PR^2{}_4]^+ \qquad (2),$$

where
$R^2$ in each case, independently of one another, denotes H, OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more $R^2$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X or —NO$_2$, and where one or two non-adjacent carbon atoms of the $R^2$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated $C_1$- to $C_6$-alkyl, $C_3$- to $C_7$-cycloalkyl, or unsubstituted or substituted phenyl, and X=halogen.

However, cations of the formulae (1) and (2) in which all four or three substituents R and $R^2$ are fully substituted by halogens are excluded, for example the tris(trifluoromethyl)methylammonium cation, the tetra(trifluoromethyl)ammonium cation or the tetra(nonafluorobutyl)ammonium cation.

Uronium cations can be described, for example, by the formula (3)

$$[(R^3R^4N)-C(=OR^5)(NR^6R^7)]^+ \qquad (3),$$

and thiouronium cations can be described by the formula (4)

$$[(R^3R^4N)-C(=SR^5)(NR^6R^7)]^+ \qquad (4),$$

where
$R^3$ to $R^7$ each, independently of one another, denote hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more of the substituents $R^3$ to $R^7$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X or —NO$_2$, and where one or two non-adjacent carbon atoms of $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated $C_1$- to $C_6$-alkyl, $C_3$- to $C_7$-cycloalkyl, or unsubstituted or substituted phenyl, and X=halogen.

Guanidinium cations can be described by the formula (5)

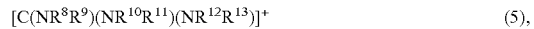

$$[C(NR^8R^9)(NR^{10}R^{11})(NR^{12}R^{13})]^+ \qquad (5),$$

where
$R^8$ to $R^{13}$ each, independently of one another, denote hydrogen, —CN, NR'$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more of the substituents $R^8$ to $R^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X or —NO$_2$, and where one or two non-adjacent carbon atoms of $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated $C_1$- to $C_6$-alkyl, $C_3$- to $C_7$-cycloalkyl, or unsubstituted or substituted phenyl, and
X=halogen.

In addition, it is possible to employ cations of the general formula (6)

$$[HetN]^+ \qquad (6)$$

where
HetN$^+$ denotes a heterocyclic cation selected from the group

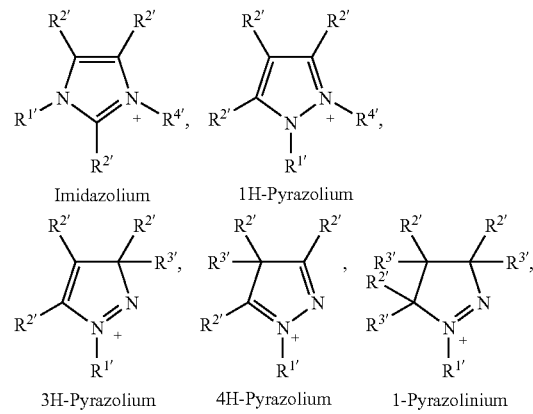

-continued

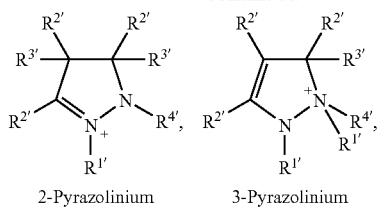

2-Pyrazolinium     3-Pyrazolinium

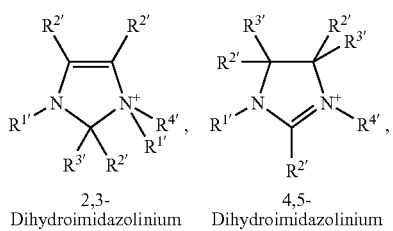

2,3-Dihydroimidazolinium     4,5-Dihydroimidazolinium

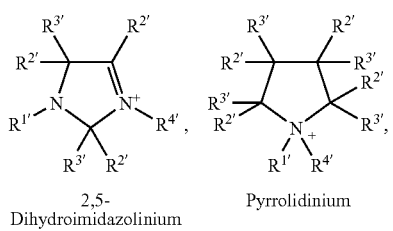

2,5-Dihydroimidazolinium     Pyrrolidinium

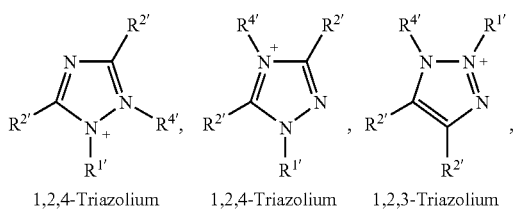

1,2,4-Triazolium     1,2,4-Triazolium     1,2,3-Triazolium

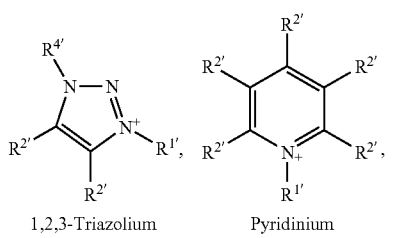

1,2,3-Triazolium     Pyridinium

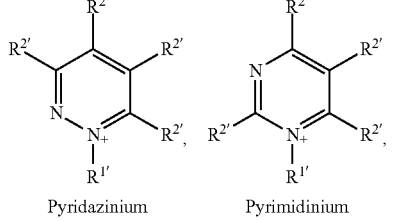

Pyridazinium     Pyrimidinium

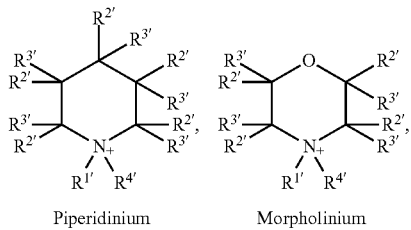

Piperidinium     Morpholinium

-continued

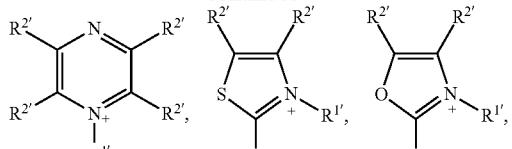

Pyrazinium     Thiazolium     Oxazolium

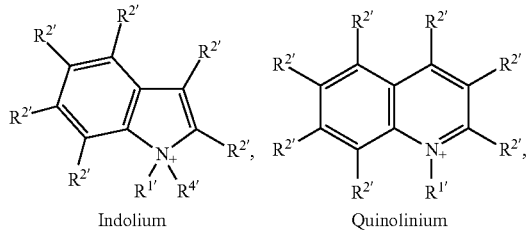

Indolium     Quinolinium

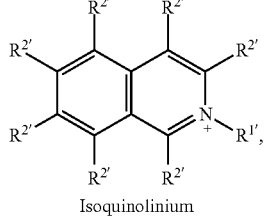

Isoquinolinium

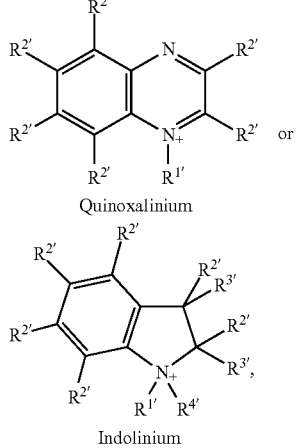

Quinoxalinium     or

Indolinium where the substituents
$R^{1'}$ to $R^{4'}$ each, independently of one another, denote
hydrogen, —CN, —OR', —NR'$_2$, —P(O)R'$_2$, —P(O)(OR')$_2$, —P(O)(NR'$_2$)$_2$, —C(O)R', —C(O)OR',
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms,
saturated, partially or fully unsaturated heteroaryl, heteroaryl-$C_1$-$C_6$-alkyl or aryl-$C_1$-$C_6$-alkyl,
where the substituents $R^{1'}$, $R^{2'}$, $R^{3'}$ and/or $R^{4'}$ together may also form a ring system,
where one or more substituents $R^{1'}$ to $R^{4'}$ may be partially or fully substituted by halogens, in particular —F and/or —Cl, or —OH, —OR', —CN, —C(O)OH, —C(O)NR'$_2$, —SO$_2$NR'$_2$, —C(O)X, —SO$_2$OH, —SO$_2$X or —NO$_2$, but where $R^{1'}$ and $R^{4'}$ cannot simultaneously be fully substituted by halogens, and where one or two non-adjacent carbon atoms of the substituents R¹' to R⁴' which are not bonded to the heteroatom may be replaced by atoms and/or atom groups selected from —O—, —S—, —S(O)—, —SO₂—, —SO₂O—, —C(O)—, —C(O)O—, —N⁺R'₂—, —P(O)R'O—, —C(O)NR'—, —SO₂NR'—, —OP(O)R'O—, —P(O)(NR'₂)NR'—, —PR'₂=N— and —P(O)R'—, where R'=H, non, partially or perfluorinated $C_1$- to $C_6$-alkyl, $C_3$- to $C_7$-cycloalkyl, or unsubstituted or substituted phenyl, and X=halogen.

For the purposes of the present invention, fully unsaturated substituents are also taken to mean aromatic substituents.

In accordance with the invention, suitable substituents R and $R^2$ to $R^{13}$ of the compounds of the formulae (1) to (5), besides hydrogen, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, iso-propyl, propyl, butyl, sec-butyl, tert-butyl, pentyl, hexyl, octyl, decyl or tetra-decyl.

Up to four substituents of the guanidinium cation [C(NR⁸R⁹)(NR¹⁰R¹¹)(NR¹²R¹³)]⁺ may also be bonded in pairs in such a way that mono-, bi- or polycyclic cations are formed.

Without restricting generality, examples of such guanidinium cations are:

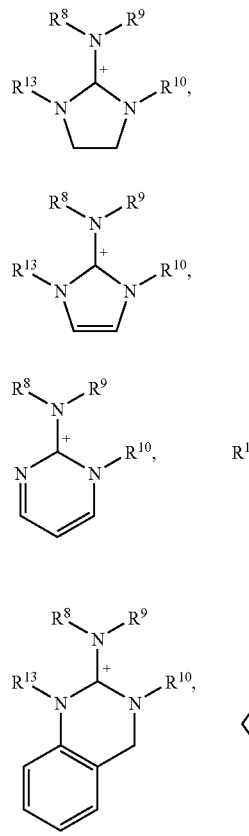
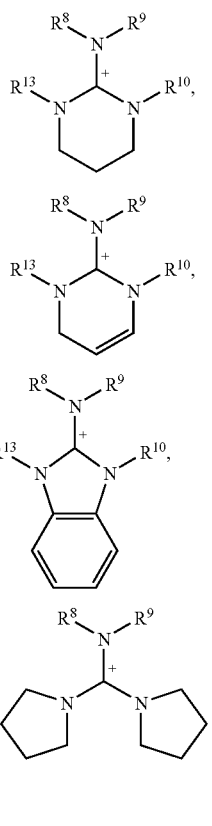
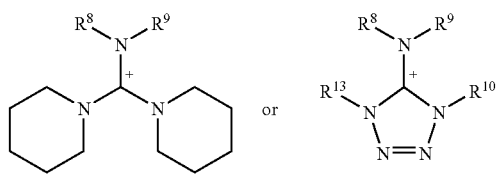

where the substituents $R^8$ to $R^{10}$ and $R^{13}$ can have a meaning or particularly preferred meaning indicated above.

If desired, the carbocyclic or heterocyclic rings of the guanidinium cations indicated above may also be substituted by $C_1$- to $C_6$-alkyl, $C_1$- to $C_6$-alkenyl, NO₂, F, Cl, Br, I, OH, $C_1$-$C_6$-alkoxy, SCF₃, SO₂CF₃, COOH, SO₂NR'₂, SO₂X' or SO₃H, where X and R' have a meaning indicated above, substituted or unsubstituted phenyl or an unsubstituted or substituted heterocycle.

Up to four substituents of the uronium cation [(R³R⁴N)—C(=OR⁵)(NR⁶R⁷)]⁺ or thiouronium cation [(R³R⁴N)—C(=SR⁵)(NR⁶R⁷)]⁺ may also be bonded in pairs in such a way that mono-, bi- or polycyclic cations are formed.

Without restricting generality, examples of such cations are indicated below, where Y=O or S:

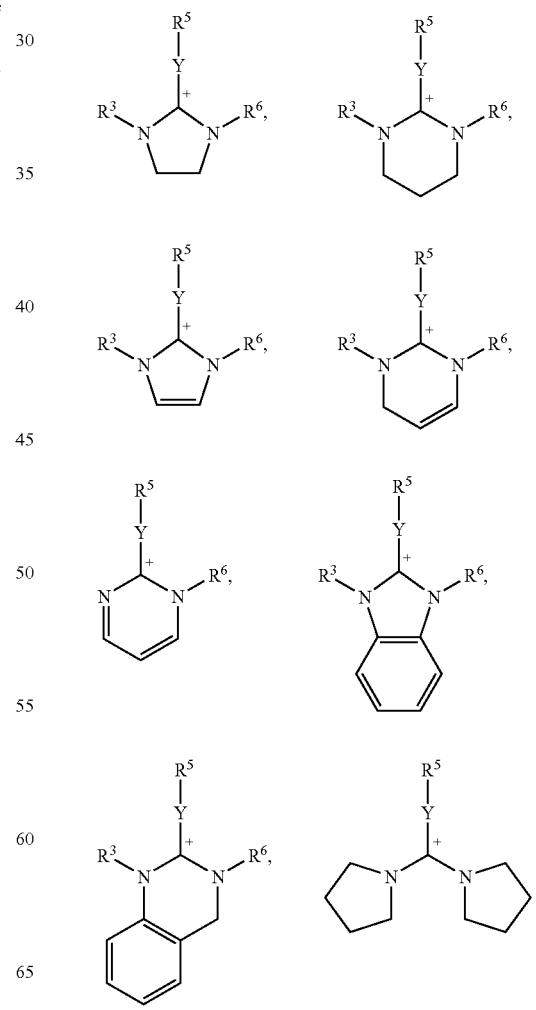

-continued

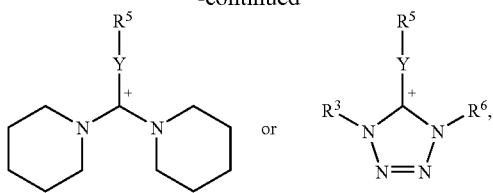

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR'_2$, $SO_2X$ or $SO_3H$ or substituted or unsubstituted phenyl or an unsubstituted or substituted heterocycle, where X and R' have a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (5) may be identical or different here. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (6), besides hydrogen, are preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl, optionally difluoromethyl, trifluoromethyl, penta-fluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, $-C_9H_{17}$, $-C_{10}H_{19}$ to $-C_{20}H_{39}$; preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, hept-ynyl, octynyl, $-C_9H_{15}$, $-C_{10}H_{17}$ to $-C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —CN, —C(O)OH, —C(O)NR'$_2$, —SO$_2$NR'$_2$, —C(O)X, —SO$_2$OH, —SO$_2$X, —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N+R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=non-, partially or perfluorinated $C_1$- to $C_6$-alkyl, $C_3$- to $C_7$-cycloalkyl or unsubstituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, NO$_2$, F, Cl, Br, I, OH, $C_1$-$C_6$-alkoxy, SCF$_3$, SO$_2$CF$_3$, COOH, SO$_2$X', SO$_2$NR"$_2$ or SO$_3$H, where X' denotes F, Cl or Br, and R" denotes a non-, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)-phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-di-hydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-di-bromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' and R'' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl or pyridinylhexyl, where the heterocycles described above may furthermore be linked to the alkylene chain in this way.

HetN$^+$ is preferably

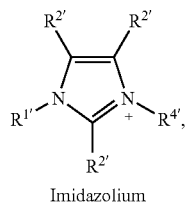
Imidazolium

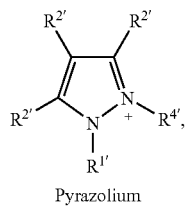
Pyrazolium

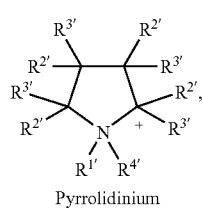
Pyrrolidinium

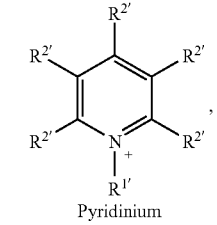
Pyridinium

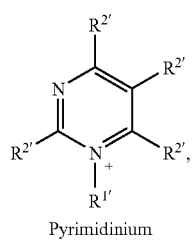
Pyrimidinium

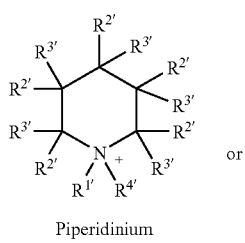
Piperidinium or

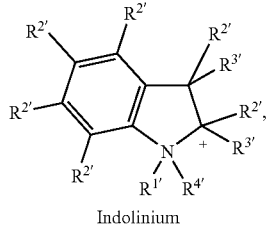
Indolinium where the substituents $R^1$ to $R^4$ each, independently of one another, have a meaning described above.

The cations of the ionic liquid according to the invention are preferably ammonium, phosphonium, guanidinium or heterocyclic cations, particularly preferably heterocyclic cations (HetN$^+$). HetN$^+$ is particularly preferably imidazolium, pyrrolidinium or pyridinium, as defined above, where the substituents $R^{1'}$ to $R^{4'}$ each, independently of one another, have a meaning described above. HetN$^+$ is very particularly preferably imidazolium, where the substituents $R^{1'}$ to $R^{4'}$ each, independently of one another, have a meaning described above.

The present invention likewise relates to processes for the preparation of ionic liquids comprising cations and anions, where the anion conforms to the formula $[(R_F)_2P(O)]_2N^-$, where $R_F$ has the meaning $(C_nF_{2n-x+1}H_x)$ where n=1-6 and x=0-4, where, for n=1, x should be 0 to 2, where compounds of the general formula (7)

$[(R_F)_2P(O)]_2NY$ (7)

in which Y=H, alkali metals, alkaline-earth metals and metals from groups 11 and 12 of the Periodic Table, are reacted with compounds of the type K$^+$A$^-$, where K$^+$ is selected from the above-mentioned cations and A$^-$=Cl$^-$, Br$^-$, I$^-$, $BF_4^-$, R'OSO$_3^-$, R'SO$_3^-$ or (R')$_2$P(O)O$^-$, where the substituents R' have a meaning described above, in a solvent or solvent mixture. A$^-$ is particularly preferably Cl$^-$, Br$^-$, I$^-$, $BF_4^-$, $HSO_4^-$ $CH_3OSO_3^-$, $C_2H_5OSO_3^-$, $CH_3SO_3^-$, $CF_3SO_3^-$, $(C_2F_5)_2P(O)O^-$ and very particularly preferably Cl$^-$, Br$^-$, $CH_3SO_3^-$, $C_2H_5OSO_3^-$ or $(C_2F_5)_2P(O)O^-$.

Y particularly preferably denotes H, alkali metals and in particular potassium or sodium.

Some of the compounds of the formula (7) are known to the person skilled in the art and can be prepared by processes as described, for example, in N. V. Pavlenko, G. I. Matuschecheva, V. Ya. Semenii, L. M. Yagupolskii, Zh. Obsh. Khim, 1985, 55, 1586-1590.

The reaction can be carried out at temperatures in the range from 0 to 150° C., preferably at 0 to 50° C. and in particular at room temperature.

Suitable solvents or solvent mixtures are water, alcohols, dialkyl ethers, esters, nitriles, dialkyl carbonates, dichloromethane or mixtures thereof. The solvent is preferably water, methanol, ethanol, i-propanol, acetonitrile, propionitrile, diethyl ether, 1,2-dimethoxyethane, dimethyl carbonate or di-ethyl carbonate.

The present invention furthermore relates to the use of the said ionic liquids as solvent or solvent additive, as phase-transfer catalyst, as extractant, as heat-transfer medium, as surface-active substance, as plasticiser, as flame retardant or as conductive salt.

In the case of the use of the said ionic liquids as solvents, these are suitable in any type of reaction known to the person skilled in the art, for example for transition-metal- or enzymecatalysed reactions, such as, for example, hydroformylation reactions, oligomerisation reactions, esterifications or isomerisations, where the said list is not exhaustive.

On use as extractant, the ionic liquid can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials, as flame retardant for a number of materials or applications, and as conductive salt in various electrochemical cells and applications, for example in galvanic cells, in capacitors or in fuel cells.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were recorded on solutions in deuterated solvents at 20° C. in a Bruker Avance 300 spectrometer with a 5 mm $^1$H/BB broad-band head with deuterium lock, unless indicated in the examples. The measurement frequencies of the various nuclei are: $^1$H: 300.13 MHz, 19F: 282.41 MHz and $^{31}$P: 121.49 MHz. The referencing method is indicated separately for each spectrum or each data set.

EXAMPLES

Example 1

Synthesis of bis(pentafluoroethyl)phosphinyl chloride

30.0 g (99.3 mmol) of bis(pentafluoroethyl)phosphinic acid and 20.7 g (99.4 mol) of phosphorus pentachloride are mixed with one another and stirred at room temperature for 30 minutes. Bis(pentafluoroethyl)phosphinyl chloride is isolated from the reaction mixture by fractional distillation. The boiling point is 118-119° C. 23.1 g of a colourless liquid are obtained. The yield is 72.6% of the calculated yield of bis(pentafluoroethyl)phosphinyl chloride.

Example 2

Synthesis of bis(pentafluoroethyl)phosphinic amide

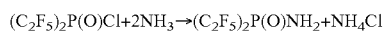

8.6 g of a 12.4% by weight solution of $NH_3$ (62.6 mmol) in dry diethyl ether are added over the course of 5 minutes with stirring at −78° C. (dry ice/ethanol bath) to a solution of 10 g (31.2 mmol) of bis(pentafluoroethyl)phosphinyl chloride in 50 ml of dry diethyl ether. The reaction mixture is warmed to room temperature and stirred for about 30 minutes. The precipitate is filtered off, and the filtrate is freed from solvent. The residue is recrystallised from a mixture of benzene and hexane (1:2), giving 5.45 g of a solid having a melting point of 28-32° C. The yield of bis(pentafluoroethyl)phosphinic amide is 58%.

$^1$H-NMR ($CD_3CN$; reference: TMS): δ (ppm): 2.28 s ($NH_2$).
$^{19}$F-NMR ($CD_3CN$; reference: $CCl_3F$, internal,): δ (ppm): −80.46 s (2$CF_3$); −124.95 d (2$CF_2$); $^2J_{P,F}$=87 Hz.
$^{31}$P-NMR ($CD_3CN$; reference: 85% $H_3PO_4$-external), δ (ppm): 0.87 quin.; $^2J_{P,F}$=87 Hz.

Example 3

Synthesis of bis(pentafluoroethyl)phosphinic imide, [($C_2F_5$)$_2$P(O)]$_2$NH

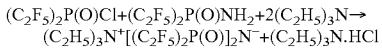

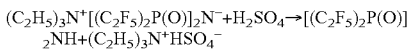

A solution of 5.54 g (17.3 mmol) of bis(pentafluoroethyl)phosphinyl chloride in 20 ml of dry diethyl ether and a solution of 3.5 g (34.6 mmol) of triethylamine in 10 ml of dry diethyl ether are added at 0° C. to a stirred solution of 5.21 g (17.3 mmol) of bis(pentafluoroethyl)phosphinic amide in 20 ml of dry diethyl ether. The reaction mixture is warmed to room temperature and stirred for a further hour. The precipitate is filtered off, and the solvent is removed in a rotary evaporator. 2 ml of concentrated sulfuric acid are added to the residue, and bis(pentafluoroethyl)phosphinic imide is distilled off under reduced pressure (7 Pa) at temperatures of 115-125° C., giving 7.3 g of a solid (melting point: 38-41° C.). The yield of bis(pentafluoroethyl)-phosphinic imide is 72.1%.

$^1$H-NMR ($CD_3CN$; reference: TMS): δ (ppm): 12.17 s (NH).
$^{19}$F-NMR ($CD_3CN$; reference: $CCl_3F$, internal): δ (ppm): −80.57 s (2$CF_3$); −125.35 d (2$CF_2$); $^2J_{P,F}$=79 Hz.
$^{31}$P-NMR ($CD_3CN$; reference: 85% $H_3PO_4$-external), δ (ppm): 1.82 quin.; $^2J_{P,F}$=78 Hz.

Example 4

Synthesis of 1-butyl-3-methylimidazolium bis[bis(pentafluoroethyl)phosphinyl]imide

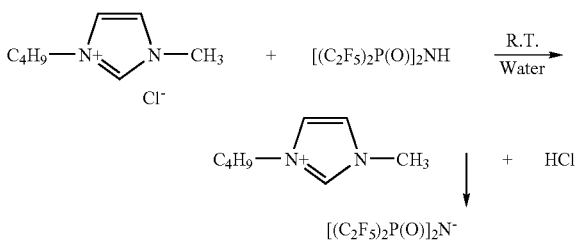

A solution of 1.7 g (9.73 mmol) of 1-butyl-3-methylimidazolium chloride in 10 ml of water is added to a solution of 5.6 g (9.57 mmol) of bis(pentafluoroethyl)phosphinic imide in 30 ml of water with stirring at room temperature. The mixture is stirred for 5 minutes. The lower liquid phase formed is separated off and washed three times with 30 ml of water. Drying under reduced pressure (7 Pa) at 90° C. gives 6.2 g of a liquid. The yield of 1-butyl-3-methylimidazolium bis[bis(pentafluoroethyl)phosphinyl]imide is 98.6%.

$^1$H-NMR ($CD_3CN$; reference: TMS): δ (ppm): 0.95 t ($CH_3$); 1.33 m ($CH_2$); 1.81 m ($CH_2$); 3.82 s ($CH_3$); 4.13 t (CH$_2$); 7.33 d,d (CH); 7.37 d,d (CH); 8.39 br. s. (CH); $^3J_{H,H}$=7.4 Hz; $^3J_{H,H}$=7.3 Hz; $J_{H,H}$=1.8 Hz.

$^{19}$F-NMR (CD$_3$CN; reference: CCl$_3$F, internal), δ (ppm): −79.89 s (2CF$_3$); −124.77 d (2CF$_2$); $^2J_{P,F}$=72 Hz.

$^{31}$P-NMR (CD$_3$CN; reference: 85% H$_3$PO$_4$—external), δ (ppm): −0.80 quin.; $^2J_{P,F}$=73 Hz.

The viscosity is 46 mm$^2$/s (20° C.).

Example 5

Synthesis of 1-ethyl-3-methylimidazolium bis[bis(pentafluoroethyl)phosphinyl]imide

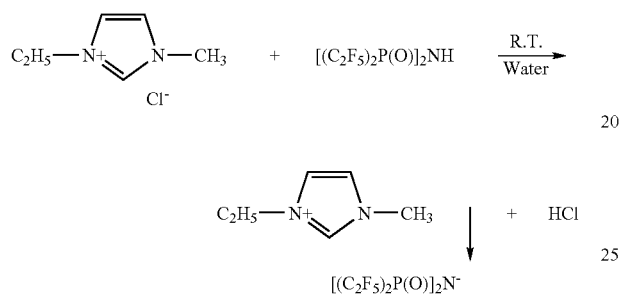

A solution of 2.52 g (17.2 mmol) of 1-ethyl-3-methylimidazolium chloride in 15 ml of water is added to a solution of 10.07 g (17.2 mmol) of bis(pentafluoroethyl)phosphinic imide in 40 ml of water with stirring at room temperature. The mixture is stirred for 5 minutes. The lower liquid phase formed is separated off and washed three times with 40 ml of water. Drying under reduced pressure (7 Pa) at 100° C. gives 9.93 g of a liquid. The yield of 1-ethyl-3-methylimidazolium bis[bis(pentafluoroethyl)phosphinyl]imide is 83%.

$^1$H-NMR (CD$_3$CN; reference: TMS): δ (ppm): 1.47 t (CH$_3$); 3.84 s (CH$_3$); 4.18 t (CH$_2$); 7.34 m (CH); 7.39 m (CH); 8.43 br. s. (CH); $^3J_{H,H}$=7.3 Hz.

$^{19}$F-NMR (CD$_3$CN; reference: CCl$_3$F, internal): δ (ppm): −80.09 s (2CF$_3$); −124.82 d (2CF$_2$); $^2J_{P,F}$=71 Hz.

$^{31}$P-NMR (CD$_3$CN; reference: 85% H$_3$PO$_4$—external): δ (ppm): −1.87 quin.; $^2J_{P,F}$=70 Hz.

The viscosity is 26 mm$^2$/s (20° C.).

Example 6

Synthesis of 1-butyl-1-methylpyrrolidinium bis[bis(pentafluoroethyl)phosphinyl]imide

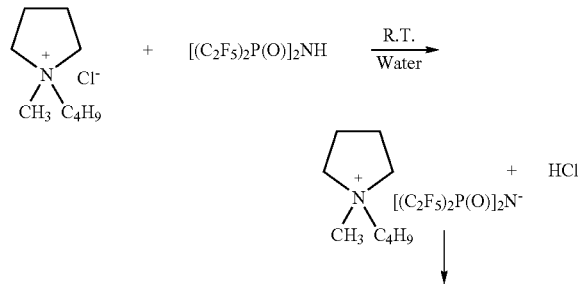

A solution of 3.03 g (17.1 mmol) of 1-butyl-1-methylpyrrolidinium chloride in 15 ml of water is added to a solution of 10.0 g (17.1 mmol) of bis(pentafluoroethyl)phosphinic imide in 40 ml of water with stirring at room temperature. The mixture is stirred for 5 minutes. The lower liquid phase formed is separated off and washed three times with 40 ml of water. Drying under reduced pressure (7 Pa) at 100° C. gives 11.03 g of a liquid. The yield of 1-butyl-1-methylpyrrolidinium bis[bis(pentafluoroethyl)phosphinyl]imide is 89%.

$^1$H-NMR (CD$_3$CN; reference: TMS): δ (ppm): 0.97 t (CH$_3$); 1.38 m (CH$_2$); 1.73 m (CH$_2$); 2.16 m (2CH$_2$); 2.95 s (CH$_3$); 3.24 m (CH$_2$); 3.41 m (2CH$_2$); $^3J_{H,H}$=7.4 Hz.

$^{19}$F-NMR (CD$_3$CN; reference: CCl$_3$F, internal): δ (ppm): −80.12 s (2CF$_3$); −124.80 d (2CF$_2$); $^2J_{P,F}$=70 Hz.

$^{31}$P-NMR (CD$_3$CN; reference: 85% H$_3$PO$_4$—external): δ (ppm): −1.98 quin.; $^2J_{P,F}$=70 Hz.

The viscosity is 69 mm$^2$/s (20° C.).

Example 7

Synthesis of 1-butyl-4-methylpyridinium bis[bis(pentafluoroethyl)phosphinyl]imide

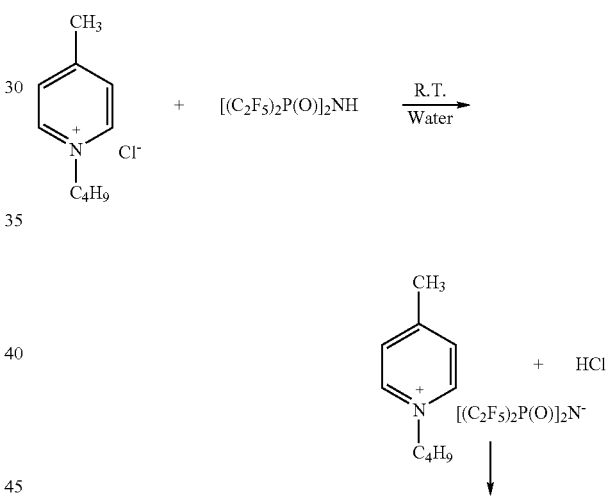

A solution of 3.02 g (16.3 mmol) of 1-butyl-4-methylpyridinium chloride in 15 ml of water is added to a solution of 9.53 g (16.3 mmol) of bis(pentafluoroethyl)phosphinic imide in 40 ml of water with stirring at room temperature. The mixture is stirred for 5 minutes. The lower liquid phase formed is separated off and washed three times with 40 ml of water. Drying under reduced pressure (7 Pa) at 100° C. gives 11.0 g of a liquid. The yield of 1-butyl-4-methylpyridinium bis[bis(pentafluoroethyl)phosphinyl]imide is 92%.

$^1$H-NMR (CD$_3$CN; reference: TMS): δ (ppm): 0.96 t (CH$_3$); 1.37 m (CH$_2$); 1.93 m (CH$_2$); 2.63 s (CH$_3$); 4.46 t (2CH$_2$); 7.83 d (2CH, A); 8.51 d (2CH, B); $^3J_{H,H}$=7.3 Hz; $^3J_{H,H}$=7.5 Hz; $^3J_{A,B}$=6.5 Hz.

$^{19}$F-NMR (CD$_3$CN; reference: CCl$_3$F, external): δ (ppm): −80.10 s (2CF$_3$); −124.85 d (2CF$_2$); $^2J_{P,F}$=71 Hz.

$^{31}$P-NMR (CD$_3$CN; reference: 85% H$_3$PO$_4$—external): δ (ppm): −1.64 quin.; $^2J_{P,F}$=71 Hz.

The viscosity is 50 mm$^2$/s (20° C.).

Example 8

Synthesis of tetra-n-butylphosphonium bis[bis(pentafluoroethyl)phosphinyl]imide

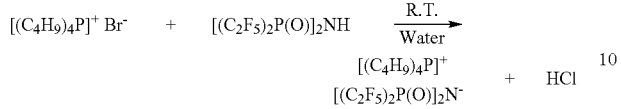

A solution of 5.97 g (17.6 mmol) of tetra-n-butylphosphonium bromide in 15 ml of water is added to a solution of 10.30 g (17.6 mmol) of bis(pentafluoroethyl)phosphinic imide in 40 ml of water with stirring at room temperature. The colourless precipitate is filtered off and washed three times with 40 ml of water. Drying under reduced pressure (7 Pa) at 50° C. gives 13.97 g of a solid. The yield of tetra-n-butylphosphonium di[bis(pentafluoroethyl)-phosphinyl]imide is 94%. The melting point is 67-68° C.

$^1$H-NMR (CD$_3$CN; reference: TMS): δ (ppm): 0.96 m (4CH$_3$); 1.38-1.62 m (8CH$_2$); 2.00-2.16 m (4CH$_2$).

$^{19}$F-NMR (CD$_3$CN; reference: CCl$_3$F, external): δ (ppm): −80.10 s (2CF$_3$); −124.83 d (2CF$_2$); $^2J_{P,F}$=69 Hz.

$^{31}$P-NMR (CD$_3$CN; reference: 85% H$_3$PO$_4$—external): δ (ppm): −1.97 quin.; $^2J_{P,F}$=69 Hz.

The invention claimed is:

1. An ionic liquid comprising cations and anions, wherein the anion conforms to the formula

[(R$_F$)$_2$P(O)]$_2$N$^-$, where R$_F$ has the meaning (C$_n$F$_{2n-x+1}$ H$_x$)
    where n=1-6 and x=0-4, where, for n=1, x is 0 to 2, and
    the cation conforms to the formula (6)

[HetN]$^+$ (6)

where
    HetN$^+$ denotes a heterocyclic cation selected from the group consisting of

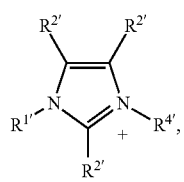

Imidazolium

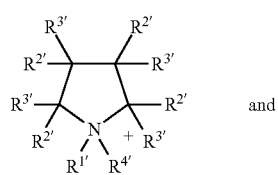

Pyrrolidinium and

Pyridinium where
R$^{1'}$ and R$^{4'}$ each, independently of one another, denote a straight-chain or branched alkyl having 1-20 C atoms, and R$^{2'}$ and R$^{3'}$ each, independently of one another, denote hydrogen, or a straight-chain or branched alkyl having 1-20 C atoms.

2. An ionic liquid according to claim 1, which has a chloride content of less than 100 ppm.

3. An ionic liquid according to claim 1, wherein R$_F$ has the meaning CF$_3$, C$_2$F$_5$, C$_3$F$_7$ or C$_4$F$_9$.

4. An ionic liquid according to claim 1, wherein the anion is [(C$_2$F$_5$)$_2$P(O)]$_2$N$^-$.

5. A process for preparing an ionic liquid according to claim 1, comprising reacting a compound of formula (7)

[(R$_F$)$_2$P(O)]$_2$NY (7)

in which Y is selected from the group consisting of H, alkali metals, alkaline-earth metals and metals from groups 11 and 12 of the Periodic Table,
    with a compound K$^+$A$^-$,
    where K$^+$ is
    a cation conforming to the formula (6)

[HetN]$^+$ (6)

where
    HetN$^+$ denotes a heterocyclic cation selected from the group consisting of

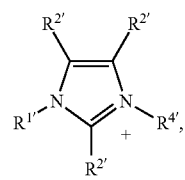

Imidazolium

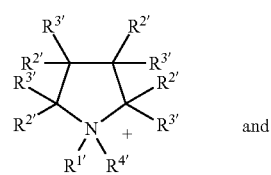

Pyrrolidinium and

Pyridinium

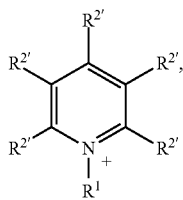

where

R$^{1'}$ and R$^{4'}$ each, independently of one another, denote a straight-chain or branched alkyl having 1-20 C atoms and R$^{2'}$ and R$^{3'}$ each, independently of one another, denote hydrogen, or a straight-chain or branched alkyl having 1-20 C atoms, and A$^-$ is Cl$^-$, Br$^-$, I$^-$, BF$_4^-$, R'OSO$_3^-$, R'SO$_3^-$ or (R')$_2$P(O)O$^-$, where R' is H, non-, partially or perfluorinated C$_1$- to C$_6$-alkyl, C$_3$- to C$_7$-cycloalkyl or unsubstituted or substituted phenyl, in a solvent or solvent mixture.

6. A process according to claim 5, wherein the reaction is carried out at a temperature of 0 to 150° C.

7. A process according to claim 5, wherein the solvent is selected from the group consisting of water, alcohols, dialkyl ethers, esters, nitriles, dialkyl carbonates, dichloromethane and mixtures thereof.

8. A solvent or solvent additive, phase-transfer catalyst, extractant, heat-transfer medium, surface-active substance, plasticizer, flame retardant or conductive salt, comprising an ionic liquid according to claim 1.

9. A compound selected from the group consisting of bis(pentafluoroethyl)phosphinic amide and bis(pentafluoroethyl)phosphinic imide.

10. An ionic liquid according to claim 1, wherein the HetN$^+$ denotes imidazolium.

11. An ionic liquid according to claim 10, wherein the anion is [(C$_2$F$_5$)$_2$P(O)]$_2$N$^-$.

12. An ionic liquid according to claim 1, wherein the HetN$^+$ denotes pyridinium.

13. An ionic liquid according to claim 1, wherein the HetN$^+$ denotes pyrrolidinium.

14. An ionic liquid according to claim 12, wherein the anion is [(C$_2$F$_5$)$_2$P(O)]$_2$N$^-$.

15. An ionic liquid according to claim 13, wherein the anion is [(C$_2$F$_5$)$_2$P(O)]$_2$N$^-$.

16. A compound according to claim 9, which is bis(pentafluoroethyl)phosphinic amide.

17. A compound according to claim 9, which is bis(pentafluoroethyl)phosphinic imide.

* * * * *